US011098374B2

(12) United States Patent
Dobrowolski

(10) Patent No.: US 11,098,374 B2
(45) Date of Patent: Aug. 24, 2021

(54) GENETIC PROFILING METHOD FOR ANIMALS

(71) Applicant: GVG GENETIC MONITORING GMBH, Leipzig (DE)

(72) Inventor: Peter Dobrowolski, Leipzig (DE)

(73) Assignee: GVG GENETIC MONITORING GMBH, Leipzig (DE)

( * ) Notice: Subject to any disclaimer, the term of this patent is extended or adjusted under 35 U.S.C. 154(b) by 0 days.

(21) Appl. No.: 15/326,926

(22) PCT Filed: Jul. 14, 2015

(86) PCT No.: PCT/EP2015/066082
§ 371 (c)(1),
(2) Date: Jan. 17, 2017

(87) PCT Pub. No.: WO2016/008894
PCT Pub. Date: Jan. 21, 2016

(65) Prior Publication Data

US 2017/0211157 A1 Jul. 27, 2017

(30) Foreign Application Priority Data

Jul. 18, 2014 (EP) .................................... 14177601

(51) Int. Cl.
*C12Q 1/6888* (2018.01)
*C12Q 1/6827* (2018.01)

(52) U.S. Cl.
CPC ......... *C12Q 1/6888* (2013.01); *C12Q 1/6827* (2013.01); *C12Q 2600/156* (2013.01)

(58) Field of Classification Search
None
See application file for complete search history.

(56) References Cited

PUBLICATIONS

Iakoubova et al. (American Physiological Society 2000 vol. 3, p. 145) (Year: 2000).*
Menottti Raymond et al. (The Journal of Heredity 1995 vol. 86 p. 319) (Year: 1995).*
Wong et al. (Neuropeptides 2002 vol. 36 p. 230) (Year: 2002).*

* cited by examiner

*Primary Examiner* — Katherine D Salmon
(74) *Attorney, Agent, or Firm* — JMB Davis Ben-David

(57) ABSTRACT

Genetic characterisation of closely related inbreds is at present only possible by means of whole genome sequencing. This is however a time-consuming process.
The invention addresses the need for a method to differentiate between closely related substrains of inbreds. The method involves analysis of at least two tandem repeat loci per chromosome. Said tandem repeat loci are characterised by high mutation rates. The amplified fragments are subsequently used to determine the alleles that are present at each amplified locus within the DNA sample.

9 Claims, No Drawings

Specification includes a Sequence Listing.

GENETIC PROFILING METHOD FOR ANIMALS

CROSS REFERENCE TO RELATED APPLICATIONS

This application is a national phase filing of International Patent Application No. PCT/EP2015/066082, filed Jul. 14, 2015, which claims priority to European Application No. 14177601.3, filed Jul. 18, 2014, both of which are herein incorporated by reference in their entireties.

REFERENCE TO SEQUENCE LISTING

The Sequence Listing submitted Jan. 17, 2017, as a text file named "37578_0050U1_Sequence_Listing.txt," created on Jan. 11, 2016, and having a size of 16,164 bytes is hereby incorporated by reference pursuant to 37 C.F.R. § 1.52(e)(5).

BACKGROUND OF THE INVENTION

A genetically modified organism (GMO) is an organism whose genetic material has been altered using genetic engineering techniques. Organisms that have been genetically modified include micro-organisms such as bacteria and yeast, insects, plants, fish, and mammals. GMOs are the source of genetically modified foods, and are also widely used in scientific research and to produce goods other than food. In drug development these animals play an important role. Not all animals that are produced are actually suited for further work. Hence, genetic characterization is of great importance.

Genetically modified mammals are an important category of genetically modified organisms. Ralph L. Brinster and Richard Palmiter developed the techniques responsible for transgenic mice, rats, rabbits, sheep, and pigs in the early 1980s, and established many of the first transgenic models of human disease, including the first carcinoma caused by a transgene. The process of genetically engineering animals is a slow, tedious, and expensive process. However, new technologies are making genetic modifications easier and more precise.

The first transgenic (genetically modified) animal was produced by injecting DNA into mouse embryos then implanting the embryos in female mice.

Genetically modified animals currently being developed can be placed into six different broad classes based on the intended purpose of the genetic modification: (i) to research human diseases (for example, to develop animal models for these diseases), (ii) to produce industrial or consumer products (fibres for multiple uses), (iii) to produce products intended for human therapeutic use (pharmaceutical products or tissue for implantation), (iv) to enrich or enhance the animals' interactions with humans (hypo-allergenic pets), (v) to enhance production or food quality traits (faster growing fish, pigs that digest food more efficiently), (vi) to improve animal health (disease resistance), (vii) research use and (viii) transgenic animals are used as experimental models to perform phenotypic and for testing in biomedical research.

Genetically modified (genetically engineered) animals are becoming more vital to the discovery and development of cures and treatments for many serious diseases. By altering the DNA or transferring DNA to an animal, one can develop certain proteins that may be used in medical treatment. Stable expressions of human proteins have been developed in many animals, including sheep, pigs, and rats. Human-alpha-1-antitrypsin which has been tested in sheep and is used in treating humans with this deficiency and transgenic pigs with human-histo-compatibility have been studied in the hopes that the organs will be suitable for transplant with less chances of rejection.

Scientists have genetically engineered several organisms, including some mammals, to include green fluorescent protein (GFP) for medical research purposes. For example fluorescent pigs have been bred in the US in 2000. These pigs were bred to study human organ transplants, regenerating ocular photoreceptor cells, neuronal cells in the brain, regenerative medicine via stem cells, tissue engineering, and other diseases. In 2011 a Japanese-American Team created green-fluorescent cats in order to find therapies for HIV/AIDS and other diseases as Feline immunodeficiency virus (FIV) is related to HIV.

In 2009, scientists in Japan announced that they had successfully transferred a gene into a primate species (marmosets) and produced a stable line of breeding transgenic primates for the first time.

Within the field known as pharming, intensive research has been conducted to develop transgenic animals that produce biotherapeutics.

In 2011, Chinese scientists generated dairy cows genetically engineered with genes for human beings to produce milk that would be the same as human breast milk.

In 2006, a pig was engineered to produce omega-3 fatty acids through the expression of a roundworm gene.

Goats have been genetically engineered to produce milk with strong spiderweb-like silk proteins in their milk.

A knockout mouse is a genetically engineered mouse in which researchers have inactivated, or "knocked out", an existing gene by replacing it or disrupting it with an artificial piece of DNA. The loss of gene activity often causes changes in a mouse's phenotype, which includes appearance, behavior and other observable physical and biochemical characteristics.

Knockout mice are important animal models for studying the role of genes which have been sequenced but whose functions have not been determined. While knockout mouse technology represents a valuable research tool, some important limitations exist. About 15 percent of gene knockouts are developmentally lethal, which means that the genetically altered embryos cannot grow into adult mice. The lack of adult mice limits studies to embryonic development and often makes it more difficult to determine a gene's function in relation to human health. In some instances, the gene may serve a different function in adults than in developing embryos. Knocking out a gene also may fail to produce an observable change in a mouse or may even produce different characteristics from those observed in humans in which the same gene is inactivated.

There is variability in the whole procedure depending largely on the strain from which the stem cells have been derived. Generally cells derived from strain 129 are used. This specific strain is not suitable for many experiments (e.g., behavioural), so it is very common to backcross the offspring to other strains. Some genomic loci have been proven very difficult to knock out. Reasons might be the presence of repetitive sequences, extensive DNA methylation, or heterochromatin. The confounding presence of neighbouring 129 genes on the knockout segment of genetic material has been dubbed the "flanking-gene effect".

Another limitation is that conventional (i.e. non-conditional) knockout mice develop in the absence of the gene being investigated. At times, loss of activity during development may mask the role of the gene in the adult state, especially if the gene is involved in numerous processes spanning development. Conditional/inducible mutation approaches are then required that first allow the mouse to develop and mature normally prior to ablation of the gene of interest.

Another serious limitation is a lack of evolutive adaptations in knockout model that might occur in wild type animals after they naturally mutate.

Congenic strains are generated in the laboratory by mating two inbred strains (usually rats or mice), and backcrossing the descendants 5-10 generations with one of the original strains, known as the recipient strain. Typically selection for either phenotype or genotype is performed prior to each backcross generation. In this manner either an interesting phenotype, or a defined chromosomal region assayed by genotype is passed from the donor strain onto an otherwise uniform recipient background. Congenic mice/rats can then be compared to the pure recipient strain to determine whether they are phenotypically different if selection was for a genotypic region, or to identify the critical genetic locus, if selection was for a phenotype.

In speed congenics offspring can be produced in as little as 5 back cross generations, through selection at each offspring generation by retaining not only the desired chromosomal fragment, but also by 'losing' the maximum amount of background genetic information from the donor strain. This is also known as 'Marker Assisted' congenics, due to the use of genetic markers, typically single nucleotide polymorphism markers (SNPs).

The process can be further aided by the superovulation of females, to produce many more eggs.

Producing genetically well-defined congenic mouse strains of high health status combines breeding and genetic analysis in one package to allow the most rapid production of congenic mice.

The problem associated with most all of the above lies in the selection of the correct animal(s) for processing. Almeida et al. (Cytotechnology (2014) 66:133-147), have made use of STR markers for analyzing and distinguishing cell lines. But, the issues addressed there are others than those in genetically modified and/or inbreed animal strains. JP 2006-314289 has made use of micro satellite markers in the context of speed congenics however, these markers were not suited for addressing the problems associated with extremely closely related inbreed animal strains. Also this Japanese work was done with two different strains. No publication mentions the use of STR-Markers for speed congenics between substrains of one inbred strain.

Further, it has so far been impossible to distinguish congenic brother/brother, brother/sister or sister/sister pairs, i.e. siblings form another. Also cell tissue specific knock outs are very difficult to characterize genetically.

SUMMARY OF THE INVENTION

The invention relates to a method of genetically identifying a non-human animal and/or genetically distinguishing two or more non-human inbred animals from one another, comprising a. obtaining at least one DNA sample to be analysed,
b. amplifying at least one short tandem repeat loci (STR loci) in the genome of said animal, wherein at least 1 chromosome is the target of said amplification,
c. evaluating the amplified fragments to determine the alleles present at each amplified locus within the DNA sample,
d. wherein the tandem repeat loci amplified lie at least 10 centimorgan (20 mega base pairs) apart, wherein the STR loci are characterized by a high mutation rate, wherein a high mutation rate herein is between 1×10-1 and 1×10-3, wherein the offspring generation shares on average an identical genome of at least, 98%.

The invention further relates to a method of genetically identifying a non-human animal and/or genetically distinguishing two or more non-human inbred animals from one another, comprising a. obtaining at least one DNA sample to be analysed,
b. amplifying at least two short tandem repeat loci (STR loci) per chromosome in the genome of said animal, wherein at least 1 in 3 chromosomes is the target of said amplification,
c. evaluating the amplified fragments to determine the alleles present at each amplified locus within the DNA sample,
d. wherein the tandem repeat loci amplified lie at least 10 centimorgan (20 mega base pairs) apart.

The invention also relates to a kit for use in a method of genetically identifying a non-human animal and/or genetically distinguishing two or more non-human inbred animals from one another, comprising a. obtaining at least one DNA sample to be analysed,
b. amplifying at least two short tandem repeat loci (STR loci) per chromosome in the genome of said animal, wherein at least 1 in 3 chromosomes is the target of said amplification,
c. evaluating the amplified fragments to determine the alleles present at each amplified locus within the DNA sample,
d. wherein the tandem repeat loci amplified lie at least 10 centimorgan (20 mega base pairs) apart,
e. comprising primers for amplifying said STR loci, wherein the primers stringently bind the chromosomal DNA flanking the STR loci.

DETAILED DESCRIPTION OF THE INVENTION

With each new generation of incestuous animals that are genetically almost identical a number of new mutations such as for instance point mutations, insertions or deletions is spontaneously created. Said number of mutations cannot be narrowed down any further. It can be assumed that this is happening in each individual. Due to their spontaneous occurrence no set of identical new mutations can be found in the same offspring generation. Analytical assessment of these genetic differences would enable a method of distinguishing these mutations on the level of the respective individual. At present this is not possible without time-consuming whole genome sequencing.

The invention solves the problem of identifying and using new mutations such that DNA regions that are potentially suitable for the evolution of new mutations are selected from the whole genome. Only a very limited amount of mutations from the entire pool of novel mutations that are present in an individual are included. Solely the mutations that had occurred in the previously defined DNA regions are detected.

Surprisingly, such DNA regions can be defined in advance. A targeted selection of such regions allows for covering of the entire genome by defining respective DNA regions in periodic intervals on the respective chromosomes. According to the invention these are DNA regions that are potentially prone to new mutations consisting of insertions and deletions. These mutations can be detected using the change in size of the respective DNA region. Preferably, such regions are DNA regions that are characterised by a moderate or high mutation rate in contrast to SNPs.

The major part of the genome, meaning DNA regions showing a potentially low mutation rate, is excluded from the analysis.

According to the invention an estimate of the mutation rate of markers is performed, which is needed for a distinction between substrains of inbreed strains. Preferably the mutation rate is in the range of $10^{-1}$ to $10^{-3}$, preferably in the range of $10^{-1}$ to $10^{-2}$. These values result from the following characteristics: With mice about three generations are generated per year, which results in about 90 to 100 generations in 30 years. Since the separation of the strain C57BL/6 in 1951 in the substrains C57BL/6J and C57BL/6N about 200 generations have passed. Significantly fewer generations of inbreeding exist between the substrains C57BL/6JCrl and C57BL/6JOlaHsd respecitvely C57BL/6NCrl and C57BL/6NTac, which originated later from C57BL/6J and C57BL/6N. If the substrains C57BL/6J and C57BL/6N show different alleles in one marker at least one mutation must occur in 200 generations. Taking into account that dipliod autosomes comprise the double amount of target chromosomes this corresponds to a mutation rate of about $4 \cdot 10^{-2}$.

For the differentiation of different alleles in the substrains C57BL/6JCrl and C57BL/6JOlaHsd or C57BL/6NCrl and C57BL/6NTac mutations need to occur in less than 50 generations. This corresponds to a mutation rate of $1 \cdot 10^{-2}$. Loci, in which several substrains show different alleles, have an even higher mutation rate.

In US 2014/0066322A1 nine STR-markers were tested for the detection of cell lines. An essential criterion for their suitability was the stability over many generations. Several markers were analyzed over 44 to 45 consecutive passages of cell lines. The shown markers did not show new alleles and therefore showed a high stability, which is characteristic for STR-markers with low mutation rate, These markers are therefore unsuitable for the present invention.

Especially such DNA regions that are selected from the markers according to the invention are of interest that are, judging from their genetic structure, potentially likely to be suitable for the evolution of insertions/deletions. These regions contain for instance microsatellites that are also called Short Tandem Repeats (STR). Such repeats are short sequences consisting of 1 to 6 bases forming a motif that is repetitively occurring similar to beads on a string. Frequent motifs are for instance $[CA]_n$, $[GAC]_n$ or $[GATA]_n$. Varying numbers of these repetitions in different strains allow differentiating one strain from another. Wittmer et al (2003) describe a method wherein a plurality of such loci was analysed and as a result enabled differentiation of different mouse strains and eventually also allowed drawing-up of a family tree of the different mouse strains. Zuo et al (2012) analysed 29 different knockout mouse strains (C57BL/6J) using STRs. It was found that among the 198 microsatellite loci that were tested 41 dinucleotide and 1 trincucleotide STR marker are polymorphic. At the same time the authors also investigated stability of the markers by analysing these 42 STR markers in 10 related individuals that stem from 3 consecutive generations. None of these 10 mice showed genetic differences in the STRs and no newly evolved heterozygous STRs were detected. This means that even polymorphic STR markers are per se not suitable for the diagnosis of individuals. In addition, it was found that data concerning dinucleotide STRs cannot be used in the context of tetranucleotide STRs. Lee et al (1999) showed in a report on the relative stability of STR markers that the dinucleotide marker $(CA)_{17}$ exhibits a roughly 10 times higher mutation rate compared to the tetranucleotide marker $(GAAA)_{17}$. Therefore it is entirely possible to find a sufficient amount of polymorphic markers among dinucleotide STRs. Polymorphic tetranucleotide STRs used for the differentiation of closely related substrains of mice are not known.

Most of the STR markers that are described in literature are markers characterised by dinucleotide repeating units. Such markers are known to be difficult to analyse due to their tendency to lead to the amplification of non-specific PCR products (also known as stutter alleles). The analysis of STRs on the basis of tetranucleotide repeating units such as for instance $(GATA)_n$ is much easier to accomplish. Almeida et al (2014) describes the application of a PCR multiplex system for the differentiation of mouse cell lines wherein 9 different tetranucleotide markers of the mouse are combined with 2 additional human STR markers. Unique DNA profiles were obtained for the different cell lines. But these cell lines originate from different mouse strains. However, three different cell lines that were generated using myeloma/hybridoma cells originated from BALB/c could be differentiated from one another using 1 marker. It is however known that cell lines stemming from myeloma and hybridoma cells show higher mutation rates compared to living animals. Hence, it is not possible to automatically conclude that based on these test results said set of markers can be used to also differentiate different substrains of BALB/c mice.

A large number of SNPs in the mouse genome has been described with regard to differentiation of mouse strains. For instance, the company Taconic offers a kit that comprises a panel of 95 SNP markers and thereby allows for the differentiation of substrains of C57BL/6 strains. However, some of these substrains only differ in 1 marker. It was not possible to differentiate between the substrains C57BL/6NTac, C57BL/6NCrl and C57BL/6NHsd because no informative/suitable SNPs could be found. Therefore, bi-allelic SNPs are suitable to allow distinguishing different mouse strains but do show obvious drawbacks in the context of differentiation of closely related mouse substrains.

Several publications describe the principle of speed congenics and disclose suitable marker sets. For example the Japanese patent application (JP 2006314289 A) describes the use of dinucleotide STRs for the differentiation of the two mouse strains CBA and C57BL/6. Likewise said two strains do not represent substrains. However no publication describes the use of STR-markers to differentiate individuals of a single inbred strain or substrain.

Different individuals of the same inbred mouse strain are almost genetically identical and are homozygous in a range up to 99.98%. A simple method that allows for the differentiation of closely related substrains originating from the same inbred strain would be advantageous. Subject of the present invention is a method that entails the multiplex STR analysis of suitable polymorphic tri or tetranucleotide STR loci.

The invention relates to a method of genetically identifying a non-human animal and/or genetically distinguishing two or more non-human inbred animals from one another, comprising a. obtaining at least one DNA sample to be analysed,
b. amplifying at least one short tandem repeat loci (STR loci) in the genome of said animal, wherein at least 1 chromosome is the target of said amplification,
c. evaluating the amplified fragments to determine the alleles present at each amplified locus within the DNA sample, d. wherein the tandem repeat loci amplified lie at least 10 centimorgan (20 mega base pairs) apart.

The invention further relates to a method of genetically identifying a non-human animal and/or genetically distinguishing two or more non-human inbred animals from one another, comprising a. obtaining at least one DNA sample to be analysed,
b. amplifying at least two short tandem repeat loci (STR loci) per chromosome in the genome of said animal, wherein at least 1 in 3 chromosomes is the target of said amplification,
c. evaluating the amplified fragments to determine the alleles present at each amplified locus within the DNA sample,
d. wherein the tandem repeat loci amplified lie at least 10 centimorgan (20 mega base pairs) apart.

Further the invention relates to a preferred method of genetically identifying a non-human animal and/or genetically distinguishing two or more non-human inbred animals from one another, comprising a. obtaining at least one DNA sample to be analysed,
b. amplifying at least one short tandem repeat loci (STR loci) in the genome of said animal, wherein at least 1 chromosome is the target of said amplification,
c. evaluating the amplified fragments to determine the alleles present at each amplified locus within the DNA sample, wherein the STR loci are characterized by a high mutation rate, wherein a high mutation rate herein is between $1\times10^{-1}$ and $1\times10^{-3}$, wherein the offspring generation shares on average an identical genome of at least, 98%.

In one embodiment the animal is selected from the group of mammals, fish, birds and reptiles.

In a preferred embodiment the animal is selected from mouse, hamster, cat, dog, primate, cow, chicken, sheep and rat.

In a preferred embodiment at least 2, 3, 4, 5, 6, 7, 8, 9, 10, 11, 12, 13, 14, 15, 16, 17, 18, 19 or 20 STR loci are amplified. In a more preferred embodiment at least at least 5, 6, 7, 8, 9, 10, 11, 12, 13, 14, 15 or 16. In the most preferred embodiment at least 14 STR loci are amplified.

In one embodiment the amplified loci lie at least 5, 10 or 20 centimorgan apart.

The DNA might be obtained by any suitable method. In one embodiment the DNA is obtained using a swab.

In another embodiment the STR loci are characterized by a high mutation rate, wherein a high mutation rate herein is between $1\times10^{-1}$ and $1\times10^{-4}$, more favourably between $1\times10^{-1}$ and $1\times10^{-3}$.

Such markers have not been described yet for mice.

The STR loci may be tetranucleotide repeats. Burgarella and Navascues (2011) showed that tetranucleotide markers exhibit a higher mutation rate than hexanucleotide markers using a combination of population data and father-son results for 110 Y-chromosomal STRs. Even lower mutation rates were determined for penta and trinucleotide STRs. Dinucleotide STRs were not included in the analysis. Two publications by Ballantyne et al (2010 and 2012) describe several fast mutating Y-STRs that show a mutation rate of $10^{-2}$ per generation. It was shown that by tendency a positive correlation exists between the mutation rate and the number of identical repeating units. Likewise it has been suggested that the sequence of the repeating unit influences the mutation rate. It was found that AAAG exhibits the highest mutation rate, followed by AGAT, AAAT and AAGG.

In another embodiment the method encompasses distinguishing animals from one another, which are an offspring generation of a breeding experiment.

In one embodiment the invention relates to a method of genetically identifying a non-human animal and/or genetically distinguishing two or more non-human inbred animals from one another wherein the parental animals of the offspring are from different strains or preferably from the same inbred strain or from different sub-strains of the same inbred strain. Said mapping can be used as a proof of origin. Likewise, such sets are suitable for the authentication of cell lines.

In a preferred embodiment the parental animals share on average an identical genome of at least, 50%, 60%, 70%, 80%. 90%, 95%, 98%, 99%, 99.5% and 99.9%.

In a more preferred embodiment the offspring generation shares on average an identical genome of at least, 50%, 60%, 70%, 80%. 90%, 95%, 98%, 99%, 99.5% and 99.9%.

The method according to the invention allows differentiating between individual animals of a single inbred strain. If the breeding is continued the method could be used to identify new substrains. This would require only a few informative markers, which could be located on few or even a single chromosome.

If the method of the invention is used for backcrossing of substrains in an inbred strain about 80 to 100 or more markers are needed to determine the genetic background. These markers should be distributed evenly on all autosomes and the X-chromosome. Markers on the Y-chromosome allow the generation of specific haplotypes and therefore a direct assignment of animals to strains or substrains.

One embodiment relates to a method wherein at least two STRs are amplified on each chromosome of the genome of each animal.

In a preferred embodiment at least 3, 4, 5, 6, 7 or more STRs are amplified on each chromosome of each animal.

In some embodiments, the at least two STR loci are selected from among the loci shown in Tables 1-4. In some embodiments, the at least two STR loci are selected from the group consisting of D1S113, D1S230, D1S311, D1S408, D1S415, D1S426, D1S448 and D1S509.

In one embodiment the invention relates to a method of genetically identifying a non-human animal and/or genetically distinguishing two or more non-human inbred animals from one another wherein the animals are mice and these are selected from the following strains: AKR, 129, C57BL/6, BALB/c, DBA; NOD, CAST, C3H, CBA, SPRET, or from different sub-strains of these strains, such as sub-strains of C57BL/6: C57BL/6J or C57BL/6N, or selected from the same sub-strains but provided by different breeders such as: C57BL/6JCrl, C57BL/6JHsdOla and C57BL/6NTac, C57BL/6NCrl, C57BL/6NHsd.

In a preferred embodiment the invention relates to a method of genetically identifying a non-human animal and/or genetically distinguishing two or more non-human inbred animals from one another wherein the animals are mice and these are selected from one of the following strains: AKR, 129, C57BL/6, BALB/c, DBA; NOD, CAST, C3H, CBA, SPRET, or from different sub-strains of these strains, such as sub-strains of C57BL/6: C57BL/6J or C57BL/6N, or selected from the same sub-strains but provided by different breeders such as: C57BL/6JCrl, C57BL/6JHsdOla and C57BL/6NTac, C57BL/6NCrl, C57BL/6NHsd.

Another embodiment of the invention relates to a method wherein the animals analysed are used in a breeding process.

In one embodiment the animals that are analysed are used in a speed congenic breeding process.

In a further embodiment the animals that are analysed are used to create a genetic knockout animal.

The invention relates to a kit for use in a method of genetically identifying a non-human animal and/or genetically distinguishing two or more non-human inbred animals from another, comprising a. obtaining at least one DNA sample to be analysed,
b. amplifying at least two short tandem repeat loci (STR loci) per chromosome in the genome of said animal, wherein at least one chromosome is the target of said amplification,
c. evaluating the amplified fragments to determine the alleles present at each amplified locus within the DNA sample,
d. wherein the tandem repeat loci amplified lie at least 10 centimorgan (20 mega base pairs) apart,
e. comprising primers for amplifying said STR loci, wherein the primers stringently bind the chromosomal DNA flanking the STR loci.

The invention further relates to a kit for use in a method of genetically identifying a non-human animal and/or genetically distinguishing two or more non-human inbred animals from another, comprising a. obtaining at least one DNA sample to be analysed,
b. amplifying at least one short tandem repeat loci (STR loci) in the genome of said animal, wherein at least 1 chromosome is the target of said amplification,
c. evaluating the amplified fragments to determine the alleles present at each amplified locus within the DNA sample, wherein the STR loci are characterized by a high mutation rate, wherein a high mutation rate herein is between $1\times10^{-1}$ and $1\times10^{-3}$, wherein the offspring generation shares on average an identical genome of at least, 98%.

In other words, the invention relates to a kit for use in one of the above methods, the kit comprising primers for amplifying at least two short tandem repeat loci (STR loci) per chromosome in the genome of said animal, wherein at least 1 in 3 chromosomes is the target of said amplification, wherein the primers stringently bind the chromosomal DNA flanking the STR loci.

The invention enables breeding of offspring with multiple heterozygous loci by using siblings with different heterozygous loci.

STR loci according to the invention can be used to perform genetic monitoring of chromosomes and to avoid gene drifting.

A special embodiment of the invention the method according to the invention enables creation of incestuous lines that are characterised by a preferably low remaining level of heterozygosity.

The respective subject matter of the invention is not only centered on Y chromosomal STR markers. The focus also lies on autosomal and gonosomal markers. Whether data concerning the human Y chromosome can be correlated to autosomal markers has not been thoroughly investigated in the scientific literature. Pinto et al (2014) question the validity of the published values of Y chromosomal mutation rates. Comparable data concerning mutation rates in animal strains that are exposed to strict conditions of inbreeding is not known.

EXAMPLES (1) Identification of Regions with High Mutation Rates

Regarding the mouse genome preferably such regions that contain tetranucleotide STRs with sequence motifs such as $(GAAA)_n$, $(CTTT)_n$, $(GATA)_n$ and $(CATA)_n$ and where at least 10 consecutive identical repeating units are present are subjected to a screening program. Version 38.1 of the C57BL/6J mouse genome as available at the National Center for Biotechnology Information (NCBI) served as the basis for the search of suitable genomic sequences. In order to conduct testing of the candidate regions primer sequences were generated using the BLAST program (http://blast.ncbi.nlm.nih.gov/Blast.cgi).

To identify regions with high mutation rates in closely related substrains identical regions are analysed using PCR and subsequently the lengths of the amplification products are determined and compared. In this context substrains are analysed where a differentiation using SNPs is only possible to a limited extent: Two animals were analysed from the substrains C57BL/6N and C57BL/6J respectively. The test animals are representatives of strains that originally had an identical label but stem from different breeders. This is indicated by using an additional name extension (Tac and Crl respectively Crl and HsdOla). Said individuals originate from substrains C57BL/6NTac and C57BL/6NCrl as well as C57BL/6JCrl and C57BL/6JHsdOla. It can be conferred that the presence of heterozygous variants based on remaining original heterozygosity can be excluded due to the extremely high inbreeding rate (>100 generations) of the substrains of C57BL/6 that were used.

Identified heterozygous STR markers have to be traced back to new mutations that have occurred and that did not turn homozygous due to gene drifting. Additionally, markers that are different in the respective sub-lines, meaning that these had been set as new mutations, are screened for.

Surprisingly, already eight different heterozygous STR loci have been identified on chromosome 01 in the analysis of 27 candidate regions comprising the sequence motifs $(GAAA)_n$ and $(CTTT)_n$ respectively. The distribution is as follows (see Table 1):

| | |
|---|---|
| C57BL/6NTac | 1 STR locus |
| C57BL/6NCrl | 1 STR locus |
| C57BL/6JCrl | 5 STR loci |
| C57BL/6JHsdOla | 1 STR locus |

The finding that 7 of the 27 candidate regions that were tested contained homozygous markers that enable differentiation of the strains C57BL/6NTac and C57BL/6NCrl was equally surprising. 4 of the 27 candidate regions show differences between the strains C57BL/6JCrl and C57BL/6JHsdOla. This high quota is even more remarkable considering that Mekada et al. (2009) failed to distinguish the 5 strains of C57BL/6N that were tested when analysing for 1446 SNPs. Therefore, the loci according to the invention are suitable for the differentiation of closely related strains.

The analysis showed that the markers listed in Table 1 represent fast mutating STR loci. They are distributed across the entire length of chromosome 1. The high number of 13 informative markers among 27 candidates (corresponding to a quota of 48%) cannot be explained with mutation rates of $10^{-2}$ to $10^{-3}$ as described for STR loci found in the human genome.

Such STR markers according to the invention do not only exist on chromosome 1. Loci such as these listed in Table 1 merely demonstrate the possibility of identifying and evaluating such DNA regions. The procedure can be applied to any chromosome found in C57BL/6 strains. Likewise, possible fields of application are not limited to C57BL/6 strains. Provided DNA regions with high mutation rates are identified, identical loci according to the invention can be used in other mouse strains and to distinguish respective substrains. It is obvious that these loci function as markers exhibiting moderate or high mutation rates in random mouse strains. The only condition is that said DNA regions exist in the respective mouse strains.

TABLE 1

Polymorphic tetranucleotide STR loci on chromosome 1

| Marker | Position MBp | Allele size (bp) C57BL/ 6NTac | C57BL/ 6NCrl | C57BL/ 6JCrl | C57BL/ 6JHsdOla |
|---|---|---|---|---|---|
| D1S113 | 20 | 286 | 278 | 278 | 278 |
| D1S203 | 29 | 301 | 301 | 301 | 301/305 |
| D1S211 | 46 | 296 | 296 | 296/300 | 296 |
| D1S220 | 60 | 495 | 491/495 | 495 | 495 |
| D1S221 | 60 | 404 | 404 | 408 | 404 |
| D1S230 | 71 | 250 | 254 | 258 | 254 |
| D1S311 | 81 | 251 | 247 | 247/251 | 247 |
| D1S408 | 94 | 347/351 | 351 | 351 | 355 |
| D1S415 | 102 | 362 | 366 | 362 | 366 |
| D1S419 | 114 | 394 | 398 | 394 | 394 |

TABLE 1-continued

Polymorphic tetranucleotide STR loci on chromosome 1

| Marker | Position MBp | Allele size (bp) C57BL/ 6NTac | C57BL/ 6NCrl | C57BL/ 6JCrl | C57BL/ 6JHsdOla |
|---|---|---|---|---|---|
| D1S426 | 121 | 189 | 189 | 193/197 | 197 |
| D1S438 | 135 | 284 | 284 | 284/288 | 284 |
| D1S445 | 150 | 488 | 488 | 488/492 | 488 |
| D1S448 | 153 | 328 | 324 | 324 | 324 |
| D1S509 | 181 | 392 | 388 | 388 | 388 |

(2) Comparative Investigation of Siblings in an Offspring Generation

In total 10 offspring of a parental couple were analysed using five markers according to the invention on chromosome 13. The animals belonged to substrain C57BL/6JCrl. The results of the analysis allow the animals to be divided into 8 groups that can be unambiguously differentiated from one another. Including additional markers makes the differentiation between animals 1 and 2 as well as 3 and 4 respectively possible without ambiguity.

TABLE 2

Polymorphic tetranucleotide STR loci on chromosome 13

| Chromosome 13 C57BL/6JCrl | Group | Marker ID Size of PCR products (bp) D13S314 | D13S406 | D13S409 | D13S501 | D13S525 |
|---|---|---|---|---|---|---|
| Animal no 1 | 1 | 347 | 307 | 407/411 | 373 | 210 |
| Animal no 2 | 1 | 347 | 307 | 407/411 | 373 | 210 |
| Animal no 3 | 2 | 347/351 | 307 | 407 | 373 | 210 |
| Animal no 4 | 2 | 347/351 | 307 | 407 | 373 | 210 |
| Animal no 5 | 3 | 347/351 | 307/311 | 407 | 373 | 210 |
| Animal no 6 | 4 | 347 | 307 | 407 | 373 | 206/210 |
| Animal no 7 | 5 | 347 | 307 | 407 | 373/377 | 210 |
| Animal no 8 | 6 | 347 | 307 | 407 | 373 | 210 |
| Animal no 9 | 7 | 347 | 307 | 407 | 369/373 | 210 |
| Animal no 10 | 8 | 347 | 307/311 | 407 | 373 | 210 |

TABLE 3

Primer sequences of selected loci according to the invention (chromosoma location according to the database entry of the genome of mouse strain C57BL/6J, version GRCm38.p2)

| Locus | Primer name | Sequence | Chromosomal location | Sequence motif |
|---|---|---|---|---|
| | | Chromosom01 | | |
| D1S113 SEQ ID NO: 1 | D1S113-F | GTGCTGGGACAGT TTGAATG | 20742230- 20742249 | $(GAAA)_n$ |
| SEQ ID NO: 2 | D1S113-R | TGCAGCAAGTGCT TTTACTCAG | 20742492- 20742471 | |
| D1S203 SEQ ID NO: 3 | D1S203-F | CACTGGAGTTCCT GGTGTGAT | 29222054- 29222074 | $(CTTT)_n$ |
| SEQ ID NO: 4 | D1S203-R | TCCTTGGGCCTCA TCAGCAA | 29222339- 29222320 | |
| D1S211 SEQ ID NO: 5 | D1S211-F | GGGTGGGTACAGC AACTCAA | 46886497- 46886516 | $(GAAA)_n$ |

TABLE 3-continued

Primer sequences of selected loci according to the invention (chromosoma location according to the database entry of the genome of mouse strain C57BL/6J, version GRCm38.p2)

| Locus | Primer name | Sequence | Chromosomal location | Sequence motif |
|---|---|---|---|---|
| SEQ ID NO: 6 | D1S211-R | AGGCAGCTTCACA GAAGAGG | 46886772-46886753 | |
| D1S220 SEQ ID NO: 7 | D1S220-F | AGTCTGGAGTCAC TTGGAACC | 60468335-60468355 | $(CTTT)_n$ |
| SEQ ID NO: 8 | D1S220-R | CCAAGACGTGGAC AACCAAAC | 60468809-60468789 | |
| D1S221 SEQ ID NO: 9 | D1S221-F | TCCCTGATTGCTTT TCCTCGT | 60966073-60966093 | $(GAAA)_n$ |
| SEQ ID NO: 10 | D1S221-R | TGGCATTTTGAGG CTGACAT | 60966464-60966445 | |
| D1S230 SEQ ID NO: 11 | D1S230-F | AGTGGGCCAGAG AACTTGGA | 71726432-71726451 | $(CTTT)_n$ |
| SEQ ID NO: 12 | D1S230-R | CCATACTGGTCCA CACTGAGA | 71726672-71726652 | |
| D1S311 SEQ ID NO: 13 | D1S311-F | GGGGTGGTTGAGT GGCTTTA | 81594474-81594493 | $(GAAA)_n$ |
| SEQ ID NO: 14 | D1S311-R | ACTTAACAGCCCT GGCTTCC | 81594699-81594680 | |
| D1S408 SEQ ID NO: 15 | D1S408-F | AGAGCATGCGATG TCTTGGC | 94213454-94213473 | $(CTTT)_n$ |
| SEQ ID NO: 16 | D1S408-R | TGTGGGGTGTCTG ACAGTTT | 94213781-94213762 | |
| D1S415 SEQ ID NO: 17 | D1S415-F | GGGTGTAGCTTGT GTTCAGC | 102869361-102869380 | $(CTTT)_n$ |
| SEQ ID NO: 18 | D1S415-R | CCCATGATTGGGC CTTCTAGT | 102869705-102869685 | |
| D1S419 SEQ ID NO: 19 | D1S419-F | ACACCCCCTCATT TTTGTGGT | 114906480-114906500 | $(CTTT)_n$ |
| SEQ ID NO: 20 | D1S419-R | ACCAGAGTTTCAC TCTCAGTGC | 114906848-114906827 | |
| D1S426 SEQ ID NO: 21 | D1S426-F | AAAGGAGGCGAG TAGGGTGA | 121856212-121856231 | $(CTTT)_n$ |
| SEQ ID NO: 22 | D1S426-R | GTACGTGGCACAA TGGGAGA | 121856382-121856363 | |
| D1S438 SEQ ID NO: 23 | D1S438-F | CTGCCCACCTACC TACCTCT | 135577365-135577384 | $(GAAA)_n$ |
| SEQ ID NO: 24 | D1S438-R | CCAGAGCCAGAAT TGCCAGA | 135577631-135577612 | |
| D1S445 SEQ ID NO: 25 | D1S445-F | CCCCGTGCTCATT ATTCTGC | 150496181-150496200 | $(CTTT)_n$ |
| SEQ ID NO: 26 | D1S445-R | GGCCATCGGTGGT CTTCAA | 150496643-150496625 | |

TABLE 3-continued

Primer sequences of selected loci according to the invention (chromosoma location according to the database entry of the genome of mouse strain C57BL/6J, version GRCm38.p2)

| Locus | Primer name | Sequence | Chromosomal location | Sequence motif |
|---|---|---|---|---|
| D1S448 SEQ ID NO: 27 | D1S448-F | TCAGTCTGCAGCA TGGCATA | 153626336-153626355 | $(GAAA)_n$ |
| SEQ ID NO: 28 | D1S448-R | TTTGCCTGGAAGC ATCCCTT | 153626644-153626625 | |
| D1S509 SEQ ID NO: 29 | D1S509-F | TCTCTGAATCCAT GAGCCGC | 181768454-181768473 | $(AAGG)_n$ $(GAAA)_n$ |
| SEQ ID NO: 30 | D1S509-R | AAGCAGCACACTA GACCGAG | 181768825-181768806 | |
| | | Chromosome 13 | | |
| D13S314 SEQ ID NO: 31 | D135314-F | TAGAGCTCTGGAC AGTGGGG | 53534213-53534232 | $(CTTT)_n$ |
| SEQ ID NO: 32 | D135314-R | GTCCTGATCAGTG GGGCTTG | 53534539-53534520 | |
| D13S406 SEQ ID NO: 33 | D135406-F | CAGCGTTTCTGCA ACCAGAG | 63422300-63422319 | $(GAAA)_n$ |
| SE ID NO: 34 | D135406-R | CCACCAGCAGGTG AGGATAC | 63422586-63422567 | |
| D13S409 SEQ ID NO: 35 | D135409-F | TACAAGGAACCCA GAGCTGC | 70302173-70302154 | $(CTTT)_n$ |
| SEQ ID NO: 36 | D135409-R | AGAAGGTGCCCTG TGAGACT | 70301787-70301806 | |
| D13S501 SEQ ID NO: 37 | D135501-F | TCCCTTTTCAGGC TTTGCCC | 96579631-96579650 | $(GAAA)_n$ |
| SEQ ID NO: 38 | D135501-R | CTGAGACTGGACC AGGGATG | 96579981-96579962 | |
| D13S525 SEQ ID NO: 39 | D135525-F | CTGACACTCTCCA CTCTCGC | 118888085-118888104 | $(GAAA)_n$ |
| SEQ ID NO: 40 | D135525-R | GAAGGATCCAGTC TCCCACC | 118888274-118888255 | |

TABLE 4

| Sequences of the amplified loci | |
|---|---|
| D1S113 SEQ ID NO: 41 | GTGCTGGGACAGTTTGAATGGTCTTCCACTCTATCACTCTGCAGA AAGAAAGAAAGAAAGAAAGAAAGAAAGAAAGAAAGAAAGAAAGAA AGAAAGAAAGAAAGAAAGAAAGAAAGAAAGAGGAAAGGAAAAAGG AAAGGAAAGGAAAAGACGAGAAAAGAAAAGAAAAGAAAAGAAAAG AAAAGAAAAGAAAAGAAAAGAAAAGAAAAGAACCTGGTATCGGTG CCAACAATATGGCTCTCTGAGTAAAAGCACTTGCTGCA |
| D1S203 SEQ ID NO: 42 | CACTGGAGTTCCTGGTGTGATGATAGATACTTGGTCTTACTTTCA GCACTTCTGATTAGTGTTGACCATGCAGCTTAAACAAAATCTCTA ATGACTTACATTAATATTTGAGATTCAGTGGTTAAAAAAAAATAA CACAAAGCTCAAAGAACTTTTTGGTTTTTTCTTTCTTTCTTTCTT TCTTTCTTTCTTTCTTTCTTTCTTTCTTTCTTTCTTTCTTTCTTT CTTTCTTTCTTTCTTTCTCAGCTAAAAGTGGAATGCCTGGGTTGC TGATGAGGCCCAAGGA |

TABLE 4-continued

| Sequences of the amplified loci | |
|---|---|
| D1S211<br>SEQ ID NO:<br>43 | GGGTGGGTACAGCAACTCAACTTTGAGATTTCACTGTAAAGTCAC<br>TTCAAAACAAAGAAAGAAAGAAAGAAAGAAAGAAAGAAAGAAAGA<br>AAGAAAGAAAGAAAGAAAGAAAGAAAGAAAGCAAGCAAGCAAGCA<br>AGCTTTCTCCCTCGTGATCTAGCTGGGAACATATTTGGTGTAAAA<br>GAAATCACTGAAGACTTTCAGGCACCAAACACTTATCAAGCCCCT<br>ACTATGTATCAAATGATACATAGTACCAAGTCCTCTTCTGTGAAG<br>CTGCCT |
| D1S220<br>SEQ ID NO:<br>44 | AGTCTGGAGTCACTTGGAACCAGTTATATTAAGCACTTACATTGT<br>GATTAAAAAAAAAGCACAAATATGCTTCTTTTATCTTTTAAAAAA<br>AGTTCTCATATGGTACCCCTATTATTCATTGAGTAGAGCATAAAT<br>TCAGCCATCCTTTCCTCTGCTTGTTATTTGGATGATTGTTTTCTT<br>TCTTTTCTTTCTTTCTTTCTTTCTTTCTTTCTTTCTTTCTTTCTT<br>TCTTTCTTTCTTTCTTTCTTTCTTTCTTTCTTTCTTTCTTTCTTT<br>TTTGAGACAGGGCTTTTCTGTGTAAGCTTGCCGCCTTCTGTACTT<br>CACTACCTCCCAGCTATTACCTTGACTCACCCATTACGTCTCAGG<br>AAACCTTTCTTGGCCCCACATAAAGAATTTGGTTTATGAAGATGC<br>ATGCTACTATAGTTACTTACAACATCACACTACTTAATTGAAAAT<br>AAAAGTTTGGTTGTCCACGTCTTGG |
| D1S221<br>SEQ ID NO:<br>45 | TCCCTGATTGCTTTTCCTCGTGGTGTTTAAAACACATATATGCAG<br>GCAAAACATCCACATACATTAAAAAAAATAATAAGAAAGAAAGAA<br>AGGAAGAAAGAAAGACTAAGAAAGAAGGAAAGAAAGAAGGAAAGA<br>AAGAAAGAAAGAAAGAAAGAAAGAAAGAAAGAAAGAAAGAAAGAA<br>AGAAAGAAAGAAAGAAAGGAAGGAAGGAAGCTGCTTACATTTGGA<br>CAATTTGAATTGATTTTATAAGGTGAATTTTCTTTAATAAGTCAC<br>CAAATTAGATATATTGAGTACTTAAACACATATGCATGCATATAC<br>ATATATAGTCTGTGGCTTATCTCTGATTTATCTTGCATACACCTT<br>CCTGTTAACACTATGTCAGCCTCAAAATGCCA |
| D1S230<br>SEQ ID NO:<br>46 | AGTGGGCCAGAGAACTTGGAAGGGTTAGAAGCTCTGTGACTCTCC<br>TCCCCATTTTTTCTTTCTTTCTTTCTCTCTTTCTTTCTTTCTTTC<br>TTTCTTTCTTTCTTTCTTTCTTTCTTTCTTTCTTTCTTTCTTTCT<br>TTCTTTCTCTTCCCACTGGCTAAGCTAAGTCTCCTAGTGGACCCC<br>TAAACAGATATGCTTCTGTGTAAAAAAAAAAAAAAAAAAATCTCA<br>GTGTGGACCAGTATGG |
| D1S311<br>SEQ ID NO:<br>47 | GGGGTGGTTGAGTGGCTTTAAAATGACTGAATACCACTCATTGTG<br>CTGGATAAGAAAGAAAGAAAGAAAGAAAGAAAGAAAGAAAGAAAG<br>AAAGAAAGAAAGAAAGAAAGAAAGAAAGAAAGAAAGAAAGAAAGA<br>AAGACGAAAACCGACAAACTGCAGTGGAAATAAATACAGCATTGC<br>AGGTTGGTGTGTGAGGCTACAGCTGGGGAAGCCAGGGCTGTTAAG<br>T |
| D1S408<br>SEQ ID NO:<br>48 | AGAGCATGCGATGTCTTGGCTAGACCATAGTTTGAAAAGCTTTGT<br>TATCAGTGGGCAGTTTTCTATGTATTGCTGCTTCTTAACTTCTAA<br>ATTCTCTTCAGTTCTTTGGCTGCTGCATCCTTTCTCATTCTCTTT<br>AGGTTTGTACCTTAAATAAAATCTGATACAACTCCTTTCTTTCTT<br>TCTTTCTTTCTTTCTTTCTTTCTTTCTTTCTTTCTTTCTTTCTTT<br>CTTTCTTTCTTTCTTTCTTTCGTTTATATAACCACAGGAAGCAGC<br>TTCGATTGACAGATTGTCTCCAGATACCAAAAAGCTATAAACTGT<br>CAGACACCCCACA |
| D1S415<br>SEQ ID NO:<br>49 | GGGTGTAGCTTGTGTTCAGCTGCAGATCAAGTTCTTGGGCTTTCT<br>TTCCTTCTTTCCTTCTTTCCTTCTTTCCTTCTTTCCTTCTTTCCT<br>TATTTCCTTCTTTCCTTCTTTCTTTCCTTCTGTCCTTCCTTCCTT<br>CCTTCCTTCCTTCCTTCCTAACTTCTTTCCTTCCTTCCCTCCCTT<br>CTTCCCTCTTTCTTCCTTCCTTTCTTTCTTTCTTTCTTTCTTTCT<br>TTCTTTCTTTCTTTCTTTCTTTCTTTCTTTCTCTTTGAAGATGGA<br>TATTACTCCCCAGATGGAGTAGGTTTGGACTCTCATTCCCTCCTT<br>TCTCATGTAACTAGAAGGCCCAATCATGGG |
| D1S419<br>SEQ ID NO:<br>50 | ACACCCCCTCATTTTTGTGGTATGTGTATGCAAATGGAAGAAGAC<br>CTATATGAGAAATTATGGGTATGAAGCCCATAAGCCAAGCTTATG<br>TTTTATTTCTCAGGCATCATCTATCTACCATTTCTTTCTTTCTTC<br>CTTCCTTTCTTTTTCTTTCTTTCTCTCTCTCTCCTTTCTTTCTTT<br>CTTTCTTTCTTTCTTTCTTTCTTTCTTTCTTTCTTTCTTTCTTTC<br>TTTCTTAACAGCTGAGAAAGTGTGGAGATATTCAGTCTAGCTGGC<br>CAGAGATCCAAATGATTGTCTTTTTCACCTAGGCCTAGGATTACA<br>GAGGAAGCTAAGCATGATGACTTTGTATATGAGCACTGAGAGTGA<br>AACTCTGGT |
| D1S426<br>SEQ ID NO:<br>51 | AAAGGAGGCGAGTAGGGTGACATTACTGTCCTAAAAATCAAGACT<br>CTTTCTTTCTTTCTTTCTTTCTTTCTTTCTTTCTTTCTTTCTTTC<br>TTTCTTTCTTTCTTTCTTTCTTTCTTTCTTTCTTTCTTTCTTTCT<br>ATCACAGAAAAAATGCTCTCCCATTGTGCCACGTAC |

TABLE 4-continued

| Sequences of the amplified loci | |
|---|---|
| D1S438 SEQ ID NO: 52 | CTAGCCAGGAAGGAGCTCTTGCTGCCCACCTACCTACCTCTCCAT<br>CTGCAAGCCTGCCTCAGTCTCAGGTGCACACTGGTTTGCCCTTGC<br>CAGCTGCTTGACAAGCTTCTCGTGAATTAAGCAGAATTAGAAGAA<br>AGAAAGAAAGAAAGAAAGAAAGAAAGAAAGAAAGAAAGAAAGAAA<br>GAAAGAAAGAAAGAAAGAAAGAAAGAAAGAACCCAGAGGAAGAAC<br>TGGGGATGTAGGAAGCACTACATCCTAGAGATTAAATTCAAATTC<br>TGGCAATTCTGGCTCTGG |
| D1S445 SEQ ID NO: 53 | CCCCGTGCTCATTATTCTGCATTATAAACAACACTTAGGATAATC<br>AACAACTTACTACCAGTCTTATAGTCCTTAAATAATTAACATATT<br>ATTCACTAGGCCAAGGAATATGGCCTAAAGTTTACAGTAATAAAA<br>GAGACAGATGCAATTTTAAGACAGAAATGCAAAGCTCTTATTCTG<br>TTTGTTGGGCTAAGTGAAGTCACAGCTTTTATCAAATGTTACTTC<br>CACTGATCTTCCTTTCTCTTTCTTTCTTTCTTTCTTTCTTTCTTT<br>CTTTCTTTCTTTCTTTCTTTCTTTCTTTCTTTATTTCTTCCTTCC<br>TTCCTTCCTTCCTTCCTTCCTTCCTTCCTTCCTTCCTTCCTCTCT<br>CTCTCTCTCTCTCTCTCTCTCTCTCTCTCTCTTTCTTTCTTTCTT<br>TCAGCACATGTCCTATGAAGAGCCACAAAGTATATAAATTTGAAG<br>ACCACCGATGGCC |
| D1S448 SEQ ID NO: 54 | TCAGTCTGCAGCATGGCATAAATCTGGTAGTACAGGCCTGTGATA<br>TGATACTGGCACTGCCAAAAAGAAAGAAAGAAAGAAAGAAAGAAA<br>GAAAGAAAGAAAGAAAGAAAGAAAGAAAGAAAGAAAGAAAGAAAG<br>AAAGAAAAGAGAAAGAGAAAATGTTCATAAAGAGGGAGAGGAGAG<br>AGAGAGAGAAAAAGAGAGAGAGAGAACACACGCAAGAGGGAAAGA<br>CTGGTTGATTGACTCAAAAAGACCTTCCTGGCCTGCCTGGGTTGG<br>AATGTCCGCTGTAGGGCAGAAGGGATGCTTCCAGGCAAA |
| D1S509 SEQ ID NO: 55 | TCTCTGAATCCATGAGCCGCCTCTCTAGCGCCCATAACTGTTCCC<br>TAAAAATAGAAGTAAAAAGCCAAGTGTGGTGGCACTTTAATACGT<br>GGGTCTCAGTGAATTCAAGATAAGTCTAGTCTACATTGCAATATT<br>GGTCTCAAAAAAAGGAAAGAAGGAAGGAAGGAAGGAAGGAAGGAA<br>GGAAGGAAGGAAGGAAGGAAGGAAGGAAGGAAGGAGAGCAACAAA<br>AGAAAGAAAGAAAGAAAGAAAGAAAGAAAGAAAGAAAGAAAGAAA<br>GAAAGAAAGAAAGAAAGAAAAGAAAGTTTGTAATGAGAATCCGAG<br>CGATCCCTTGAAATAAGGAAGTGGGAAGGAAGACTCTCTCGGTCT<br>AGTGTGCTGCTT |
| D13S314 SEQ ID NO: 56 | TAGAGCTCTGGACAGTGGGGGCTCCTACACCCTCATAGCACAGAA<br>TTGTGTTTGTCACCTTCACTCTGAGCACTTGGCACTTTCTTTCTT<br>TCTTTCTTTCTTTCTTTCTTTCTTTCTTTCTTTCTTTCTTTCTTT<br>CTTTCTTTCTTTCTTTCTTTCTTTCTTTCTTATGTCCAATTCTCT<br>ATGAACTGTAAGCCTCACAAATGTAATATGTATGTCTTTTATGTG<br>CTGAATTTGCACCTGTGCTTTATCCGTAGGACGTTTTACATTTTG<br>TCCTTCCTACTCTTGGAGTGTCCTCTTGGGGTGATATCAAGCCCC<br>ACTGATCAGGAC |
| D13S406 SEQ ID NO: 57 | CAGCGTTTCTGCAACCAGAGGGGATGGTCTCCAAAAGAAGACAAG<br>GGATGTTTTAAATATAAGAAAGAAAGAAAGAAAGAAAGAAAGAAA<br>GAAAGAAA<br>GAAAGAAAGAAAGAAAGAAAGGAAGAAAGGAAGGAAGGAAGAAAG<br>AAAGAAATCTTTGTTTCTTCCTAATAAAAAATAAAAACAATCATA<br>TTCCCAGAAGTATCTTCATGTTTTCCATAGGGAAGCACCAGATAC<br>TACCCTGACCTGCCTCATGATTTCTCTCTTCTAAGTATCCTCACC<br>TGCTGGTGG |
| D13S409 SEQ ID NO: 58 | TACAAGGAACCCAGAGCTGCCCTGATGTGTGGTTTCTTTTCTCTT<br>TCTTTCTTTCTTTCTTTCTTTCTTTCTTTCTTTCTTTCTTTCTTT<br>CTTTCTTTCTTTCTTTCTTTCTTTCTTTCTTTCTTTCTTTCTTAA<br>GATTTATTTATTTATTTTATGTGAGTACAGGGTTACTGTCTTCAG<br>ACATACCAGAAGAGGGCATTGGAACTCATTACAAATGGTTGTGAG<br>CCATCATGTGGTTTCTGGGAATTGAACTCAGGACCTCTGGAAGAG<br>CATTTAGTGCTCTTAACCACTGAGCCATCTCACCATCCCCTGCTT<br>TGTGGTTTCTAGGTTGGGAGAATGCTGAGAGTCTGTGGTACTGGT<br>GCATCTGAGTCTCACAGGGCACCTTCT |
| D13S501 SEQ ID NO: 59 | TCCCTTTTCAGGCTTTGCCCTCAGATACAGTTGATGCAGGTTAAT<br>TTTATCCTCCCCTCTTCTGTCATAGTTCTTGTTTATTTGTAACTT<br>CTGTTCTCCCTCCATCTCTTCTCCTTGGTTTGTTACATTCTTTGC<br>TGACTTTACTTCAGTTTAACTTCAACTTTGGCTGCCCTAAACTCT<br>TTGTAGTGCCCAATTGAAGAAAGAAAGAAAGAAAGAAAGAAAGAA<br>AGAAAGAAAGAAAGAAAGAAAGAAAGAAAGAAAGAAAGAAAGAAA<br>GAAAGAGGAAAGGAACAAGAACTTATTGATTGCTTTTTCATATCA<br>GTTAGTATAAACTGATCATCCCTGGTCCAGTCTCAG |

TABLE 4-continued

| Sequences of the amplified loci | |
|---|---|
| D13S525 SEQ ID NO: 60 | CTGACACTCTCCACTCTCGCACACTCCTTCCTTAGAGAAAGAAAG AAAGAAAGAAAGAAAGAAAGAAAGAAAGAAAGAAAGAAAGAAAGA AAGAAAGAAAGAAAGAAAGAAAGAAAGAAAGAAGTTGCTCAGGGA TTTGATTTACTGATTACCTGACTGGCTTAGAAATAGGTGGGAGAC TGGATCCTTC |

(3) Differentiation of Substrains of C57BL/6

In total 9 different commercially available substrains of C57BL6 were analysed using fourteen markers according to the invention on chromosome 1. The results demonstrate that each of these substrains can be unambiguously differentiated from one another (see Table 5).

TABLE 5

Analysis of C57BL/6-substrains by fourteen polymorphic tetranucleotide STR loci on chromosome 1

| | Position, | C57/BL6-Substrain | | | | | | | | |
|---|---|---|---|---|---|---|---|---|---|---|
| Marker | MBp | JCrl | JRj | JOlaHsd | JRccHsd | JBomTac | NRj | NTac | NHsd | NCrl |
| D1S113 | 20 | 278 | 278 | 278 | 282 | 278 | 278/282 | 286 | 278 | 278 |
| D1S203 | 29 | 301 | 301 | 301/305 | 297 | 297 | 301 | 301 | 305 | 301 |
| D1S220 | 60 | 495 | 495 | 495 | 499 | 491 | 495 | 495 | 495 | 491/495 |
| D1S221 | 60 | 408 | 408 | 404 | 404 | 404 | 404 | 404 | 404 | 404 |
| D1S230 | 71 | 258 | 258 | 254 | 254 | 254 | 254 | 250 | 254 | 254 |
| D1S311 | 81 | 247/251 | 247 | 247 | 247 | 251 | 251 | 251 | 247 | 247 |
| D1S408 | 94 | 351 | 351 | 355 | 355 | 351 | 351 | 347/351 | 355 | 351 |
| D1S415 | 102 | 362 | 362 | 366 | 362 | 362 | 362/366 | 362 | 362 | 366 |
| D1S419 | 114 | 294 | 294 | 294 | 294 | 294 | 298 | 294 | 294 | 298 |
| D1S426 | 121 | 193/197 | 193 | 197 | 193 | 193 | 189 | 189 | 189 | 189 |
| D1S438 | 135 | 284/288 | 288 | 284 | 284 | 280 | 284 | 284 | 284 | 284 |
| D1S445 | 150 | 488/492 | 488 | 488 | 488 | 484 | 488 | 488 | 488 | 488 |
| D1S448 | 153 | 324 | 324 | 324 | 324 | 320 | 328 | 328 | 324 | 324 |
| D1S509 | 181 | 388 | 388 | 388 | 392 | 388 | 392 | 392 | 388 | 388 |

Differentiation of Offspring

As shown in Table 2, using markers according to the invention enable the identification of different heterozygous loci in offspring of a parental couple. These are suitable to differentiate closely related individuals from one another.

The surprisingly high variety of such highly variable loci that are apparently scattered in large amounts across all chromosomes as well as the unexpectedly high frequency of occurrence of heterozygous markers show that the genetic monitoring system according to the invention constitutes a dynamic process wherein constantly new markers are being created that in turn replace a preceding new marker.

Breeding of Multi-Heterozygous Individuals

A special embodiment of the invention enables breeding of offspring with multiple heterozygous loci by using siblings with different heterozygous loci. Animals 1 and 5 (see Table 2) can be selected as one breeding couple whereas animals 6 and 7 can be selected as the second breeding couple. Offspring stemming from these two breeding couples can in turn be bred such that animals are born that contain a number of heterozygous loci on chromosome 13. This can be done likewise with heterozygous markers on other chromosomes. The selection of suitable parents for maintaining the variety of present heterozygous loci can be facilitated by using respective software programs. Multi-heterozygous individuals can be used for novel breeding strategies. Possible applications will be described hereinafter.

Avoidance of Gene Drifting

Starting out from silent mutations occurring with defined regularity wherein said occurrence in itself is a very rare event, one can further assume that a certain mutation occurs on only one of the two chromosomes. As a result, the pair of chromosomes does always show two homologous regions but these differ entirely with regard to occurrence and clustering of mutations (point mutations, insertions, deletions).

Different alleles on single homologous regions of a respective pair of chromosomes of multi-heterozygous animals can be used in differentiation analysis experiments when employing polymorphic markers according to the invention. It is therefore possible to unambiguously differentiate the respective homologous region from one another on each of the two chromosomes. Systematic application of the selection strategy with regard to maintaining the state of heterozygosity results in random new mutations that are in proximity to a locus according to the invention being retained in the gene pool. At the same time the wild type is being retained on the homologous region of the other chromosome of the respective pair of chromosomes. Said wild type is defined through the other allele of the heterozygous locus. In such regions according to the invention gene drifting is avoided since evolution of homozygous regions and the phenotypic manifestation of recessive mutations is stopped.

Use of numerous different polymorphic markers that are distributed across an entire chromosome in uniform distances allow for genetic monitoring of the respective chromosome and to avoid gene drifting for said entire chromosome. In the case of substrain C57BL/6JCrl the following heterozygous loci can be used: D1S211, D1S311, D1S426, D1S438 and D1S456 (see Table 1). These are distributed on chromosome 1 and localized at positions 46 Mbp, 81 Mbp, 121 Mbp, 135 Mbp and 151 Mbp. Such informative heterozygous loci can be identified on every single chromosome. Using a respective computer program to monitor individuals of an offspring generation could enable preselection of animals for further breeding with the aim of avoiding gene drifting on the entire genome.

Use of Multi-Heterozygous Individuals for Subsequent Breeding of Homozygous Animals In order to create incestuous lines characterised by a preferably low remaining level of heterozygosity multi-heterozygous individuals can be bred and offspring can be selected wherein one of the alleles of a heterozygous marker according to the invention is fixed and wherein the other allele is eliminated from the gene pool. As a result only the silent mutations that are linked to the fixed allele are retained in the gene pool. The respective homologous sequences on the second chromosome that are enriched with other silent mutations are eliminated from the gene pool. As a result offspring are created where the remaining level of residual heterozygosity is effectively zero. At present no breeding method is known that allows obtaining such a low value.

In the case of the test animal that originates from substrain C57BL/6JCrl the following loci are suitable: D1S211, D1S311, D1S426, D1S438 and D1S456 (see Table 1). These are located on chromosome 1 in uniform distances and localized at the following positions: 46 Mbp, 81 Mbp, 121 Mbp, 135 Mbp and 151 Mbp respectively. Chromosome 1 comprises 195 Mbp in total. Targeted selection aiming for homozygosity of these loci allows enables reduction of the rate of remaining heterozygosity of chromosome 1 to zero.

Differentiating Newly Created Sub-Lines of Inbreds

Markers according to the invention exhibiting moderate to high mutation rates already exist in the genome since the beginning of the breeding. Even without direct selection a temporary heterozygous marker turns within a few generations again into a homozygous marker. Therein the allele of the newly fixed marker can differ from the original marker of the parental generation. Therefore loci according to the invention that exhibit moderate to high mutation rates are generally suitable as markers in order to be able to differentiate newly created sub-lines from one another already after a few generations of separate breeding. For instance, a proof of origin can be performed for strains that carry an identical label but originate from different breeders. Strain C57BL/6N originating from Taconic (Tac) and Carles River Laboratories (Crl) can be easily differentiated using the following loci: D1S113, D1S320, D1S311, D1S419, D1S448 and D1S509 (see STR markers listed in Table 1). By targeted selection of C57BL/6NCrl offspring for homozygosity of allele 347 (locus D1S408) an additional informative marker for the differentiation of the two substrains can already be obtained within one generation. Similar potential exists in the case of the two substrains of C57BL/6J that were tested (see data presented in Table 1). In contrast to C57/6N a wider range of heterozygous markers can be fixed as homozygous in the selection process.

Another special embodiment allows for multi-heterozygous individuals to be used for targeted evolution of distinguishable sub-lines. Randomly available silent mutations are thereby also rendered homozygous wherein one sub-line is selected for retaining one allele and the second sub-line is selected for retaining the second allele. After fixing the different alleles the substrains can be unambiguously differentiated from one another. Such sub-lines could be used for the identification of respective QTL provided mutations that could impact phenotypical features are present in these DNA regions. Comparative genetic characterisation analysis can yield a prediction of the chromosomal location. Such a strategy can be used to identify QTLs comprising two or more genes in the context of genetically modified strains.

Another special embodiment of the invention employs such loci in order to differentiate identical DNA regions of a chromosome from one another between different substrains, for instance in the case of the two substrains C57BL/6J and C57BL/6N. The genetic background of a chromosome can be verified when using a number of distinguishable loci that are evenly distributed along a chromosome. Such markers can be used for performing a method called "Speed Congenics" in the context of closely related substrains. In case chromosome 1 of strain C57BL/6NTac is to be distinguished from chromosome 1 of C57BL/6JHsdOla the following markers are suitable: D1S113, D1S230, D1S311, D1S408, D1S415, D1S426, D1S448 and D1S509 (see Table 1).

The invention claimed is:

1. A method of genetically distinguishing non-identical mice from the same substrain of an offspring generation of the same strain from one another, wherein the offspring generation shares on average an identical genome of at least 99.5%, the method comprising:

(a) obtaining from each mouse at least one DNA sample to be analysed, (b) screening for and identifying in said DNA sample tetranucleotide short tandem repeat loci (STR loci) which comprise sequences selected from $(GAAA)_n$, $(CTTT)_n$, $(GATA)_n$ and $(CATA)_n$, wherein n is ≥10, and which have been previously observed to show a high mutation rate between $1\times10^{-1}$ and $1\times10^{-3}$ per STR loci per generation;

(c) amplifying at least one short tandem repeat loci (STR loci) identified in (b) in the genome of said mice, wherein at least one chromosome is the target of said amplification to produce an amplified fragment, (d) evaluating each amplified fragment to determine alleles present at each amplified locus within the DNA sample, and determining and comparing the length of said alleles present at each amplified locus, and (e) distinguishing non-identical mice from the same substrain of an offspring generation of the same strain from one another by detecting in said DNA sample from each mouse the presence of alleles with different lengths of said STR loci with a high mutation rate between $1\times10^{-1}$ and $1\times10^{-3}$ per STR loci per generation.

2. The method according to claim 1, wherein the mice are an offspring generation of a breeding experiment.

3. The method according to claim 1, wherein at least two STRs are amplified on a chromosome of the genome of each mouse.

4. The method according to claim 1, wherein at least 3, 4, 5, 6, 7, or more STRs are amplified on a chromosome of each mouse.

5. The method according to claim 1, wherein the mice are selected from the following strains: AKR, 129, C57BL/6, BALB/c, DBA, NOD, CAST, C3H, CBA, SPRET, or from different sub-strains of these strains.

6. The method according to claim 1, wherein the mice analysed are used in a breeding process.

7. The method according to claim 1, wherein the mice analysed are used in a speed congenic breeding process.

8. The method according to claim 1, wherein the mice analysed are used to generate knockout mice.

9. The method according to claim 1, wherein the mice from the same substrain of an offspring generation share on average an identical genome of at least 99.9%.

* * * * *

SEQUENCE LISTING

```
<160> NUMBER OF SEQ ID NOS: 60

<210> SEQ ID NO 1
<211> LENGTH: 20
<212> TYPE: DNA
<213> ORGANISM: Mouse

<400> SEQUENCE: 1

gtgctgggac agtttgaatg                                              20


<210> SEQ ID NO 2
<211> LENGTH: 22
<212> TYPE: DNA
<213> ORGANISM: Mouse

<400> SEQUENCE: 2

tgcagcaagt gcttttactc ag                                           22


<210> SEQ ID NO 3
<211> LENGTH: 21
<212> TYPE: DNA
<213> ORGANISM: Mouse
```

<400> SEQUENCE: 3
cactggagtt cctggtgtga t 21

<210> SEQ ID NO 4
<211> LENGTH: 20
<212> TYPE: DNA
<213> ORGANISM: Mouse

<400> SEQUENCE: 4
tccttgggcc tcatcagcaa 20

<210> SEQ ID NO 5
<211> LENGTH: 20
<212> TYPE: DNA
<213> ORGANISM: Mouse

<400> SEQUENCE: 5
gggtgggtac agcaactcaa 20

<210> SEQ ID NO 6
<211> LENGTH: 20
<212> TYPE: DNA
<213> ORGANISM: Mouse

<400> SEQUENCE: 6
aggcagcttc acagaagagg 20

<210> SEQ ID NO 7
<211> LENGTH: 21
<212> TYPE: DNA
<213> ORGANISM: Mouse

<400> SEQUENCE: 7
agtctggagt cacttggaac c 21

<210> SEQ ID NO 8
<211> LENGTH: 21
<212> TYPE: DNA
<213> ORGANISM: Mouse

<400> SEQUENCE: 8
ccaagacgtg gacaaccaaa c 21

<210> SEQ ID NO 9
<211> LENGTH: 21
<212> TYPE: DNA
<213> ORGANISM: Mouse

<400> SEQUENCE: 9
tccctgattg cttttcctcg t 21

<210> SEQ ID NO 10
<211> LENGTH: 20
<212> TYPE: DNA
<213> ORGANISM: Mouse

<400> SEQUENCE: 10
tggcattttg aggctgacat 20

<210> SEQ ID NO 11
<211> LENGTH: 20
<212> TYPE: DNA
<213> ORGANISM: Mouse

<400> SEQUENCE: 11
agtgggccag agaacttgga 20

<210> SEQ ID NO 12
<211> LENGTH: 21
<212> TYPE: DNA
<213> ORGANISM: Mouse

<400> SEQUENCE: 12
ccatactggt ccacactgag a 21

<210> SEQ ID NO 13
<211> LENGTH: 20
<212> TYPE: DNA
<213> ORGANISM: Mouse

<400> SEQUENCE: 13
ggggtggttg agtggcttta 20

<210> SEQ ID NO 14
<211> LENGTH: 20
<212> TYPE: DNA
<213> ORGANISM: Mouse

<400> SEQUENCE: 14
acttaacagc cctggcttcc 20

<210> SEQ ID NO 15
<211> LENGTH: 20
<212> TYPE: DNA
<213> ORGANISM: Mouse

<400> SEQUENCE: 15
agagcatgcg atgtcttggc 20

<210> SEQ ID NO 16
<211> LENGTH: 20
<212> TYPE: DNA
<213> ORGANISM: Mouse

<400> SEQUENCE: 16
tgtggggtgt ctgacagttt 20

<210> SEQ ID NO 17
<211> LENGTH: 20
<212> TYPE: DNA
<213> ORGANISM: Mouse

<400> SEQUENCE: 17
gggtgtagct tgtgttcagc 20

<210> SEQ ID NO 18
<211> LENGTH: 21
<212> TYPE: DNA
<213> ORGANISM: Mouse

<400> SEQUENCE: 18
cccatgattg ggccttctag t 21

<210> SEQ ID NO 19
<211> LENGTH: 21
<212> TYPE: DNA
<213> ORGANISM: Mouse

<400> SEQUENCE: 19
acaccccctc atttttgtgg t 21

<210> SEQ ID NO 20
<211> LENGTH: 22
<212> TYPE: DNA
<213> ORGANISM: Mouse

<400> SEQUENCE: 20
accagagttt cactctcagt gc 22

<210> SEQ ID NO 21
<211> LENGTH: 20
<212> TYPE: DNA
<213> ORGANISM: Mouse

<400> SEQUENCE: 21
aaaggaggcg agtagggtga 20

<210> SEQ ID NO 22
<211> LENGTH: 20
<212> TYPE: DNA
<213> ORGANISM: Mouse

<400> SEQUENCE: 22
gtacgtggca caatgggaga 20

<210> SEQ ID NO 23
<211> LENGTH: 20
<212> TYPE: DNA
<213> ORGANISM: Mouse

<400> SEQUENCE: 23
ctgcccacct acctacctct 20

<210> SEQ ID NO 24
<211> LENGTH: 20
<212> TYPE: DNA
<213> ORGANISM: Mouse

<400> SEQUENCE: 24
ccagagccag aattgccaga 20

<210> SEQ ID NO 25
<211> LENGTH: 20
<212> TYPE: DNA
<213> ORGANISM: Mouse

<400> SEQUENCE: 25
ccccgtgctc attattctgc 20

<210> SEQ ID NO 26
<211> LENGTH: 19
<212> TYPE: DNA
<213> ORGANISM: Mouse

<400> SEQUENCE: 26
ggccatcggt ggtcttcaa 19

<210> SEQ ID NO 27
<211> LENGTH: 20
<212> TYPE: DNA
<213> ORGANISM: Mouse

<400> SEQUENCE: 27
tcagtctgca gcatggcata 20

<210> SEQ ID NO 28
<211> LENGTH: 20
<212> TYPE: DNA
<213> ORGANISM: Mouse

<400> SEQUENCE: 28
tttgcctgga agcatccctt 20

<210> SEQ ID NO 29
<211> LENGTH: 20
<212> TYPE: DNA
<213> ORGANISM: Mouse

<400> SEQUENCE: 29
tctctgaatc catgagccgc 20

<210> SEQ ID NO 30
<211> LENGTH: 20
<212> TYPE: DNA
<213> ORGANISM: Mouse

<400> SEQUENCE: 30
aagcagcaca ctagaccgag 20

<210> SEQ ID NO 31
<211> LENGTH: 20
<212> TYPE: DNA
<213> ORGANISM: Mouse

<400> SEQUENCE: 31
tagagctctg gacagtgggg 20

<210> SEQ ID NO 32
<211> LENGTH: 20
<212> TYPE: DNA
<213> ORGANISM: Mouse

<400> SEQUENCE: 32
gtcctgatca gtggggcttg 20

<210> SEQ ID NO 33
<211> LENGTH: 20
<212> TYPE: DNA
<213> ORGANISM: Mouse

<400> SEQUENCE: 33
cagcgtttct gcaaccagag 20

<210> SEQ ID NO 34
<211> LENGTH: 20
<212> TYPE: DNA
<213> ORGANISM: Mouse

<400> SEQUENCE: 34
ccaccagcag gtgaggatac 20

<210> SEQ ID NO 35
<211> LENGTH: 20
<212> TYPE: DNA
<213> ORGANISM: Mouse

<400> SEQUENCE: 35
tacaaggaac ccagagctgc 20

<210> SEQ ID NO 36
<211> LENGTH: 20
<212> TYPE: DNA
<213> ORGANISM: Mouse

<400> SEQUENCE: 36
agaaggtgcc ctgtgagact 20

<210> SEQ ID NO 37
<211> LENGTH: 20
<212> TYPE: DNA
<213> ORGANISM: Mouse

<400> SEQUENCE: 37
tcccttttca ggctttgccc 20

<210> SEQ ID NO 38
<211> LENGTH: 20
<212> TYPE: DNA
<213> ORGANISM: Mouse

<400> SEQUENCE: 38
ctgagactgg accagggatg 20

<210> SEQ ID NO 39
<211> LENGTH: 20
<212> TYPE: DNA
<213> ORGANISM: Mouse

<400> SEQUENCE: 39
ctgacactct ccactctcgc 20

<210> SEQ ID NO 40
<211> LENGTH: 20
<212> TYPE: DNA
<213> ORGANISM: Mouse

<400> SEQUENCE: 40
gaaggatcca gtctcccacc 20

<210> SEQ ID NO 41
<211> LENGTH: 263
<212> TYPE: DNA
<213> ORGANISM: Mouse

<400> SEQUENCE: 41
gtgctgggac agtttgaatg gtcttccact ctatcactct gcagaaagaa agaaagaaag 60
aaagaaagaa agaaagaaag aaagaaagaa agaaagaaag aaagaaagaa agaaagaaag 120
aggaaaggaa aaaggaaagg aaaggaaaag acgagaaaag aaaagaaaag aaaagaaaag 180
aaaagaaaag aaaagaaaag aaaagaaaag aacctggtat cggtgccaac aatatggctc 240
tctgagtaaa agcacttgct gca 263

<210> SEQ ID NO 42
<211> LENGTH: 286
<212> TYPE: DNA
<213> ORGANISM: Mouse

<400> SEQUENCE: 42
cactggagtt cctggtgtga tgatagatac ttggtcttac tttcagcact tctgattagt 60
gttgaccatg cagcttaaac aaaatctcta atgacttaca ttaatatttg agattcagtg 120
gttaaaaaaa aataacacaa agctcaaaga actttttggt tttttctttc tttctttctt 180
tctttctttc tttctttctt tctttctttc tttctttctt tctttctttc tttctttctt 240
tctcagctaa aagtggaatg cctgggttgc tgatgaggcc caagga 286

<210> SEQ ID NO 43
<211> LENGTH: 276
<212> TYPE: DNA
<213> ORGANISM: Mouse

<400> SEQUENCE: 43
gggtgggtac agcaactcaa ctttgagatt tcactgtaaa gtcacttcaa aacaaagaaa 60
gaaagaaaga aagaaagaaa gaaagaaaga aagaaagaaa gaaagaaaga aagaaagaaa 120
gcaagcaagc aagcaagctt tctccctcgt gatctagctg ggaacatatt tggtgtaaaa 180
gaaatcactg aagactttca ggcaccaaac acttatcaag cccctactat gtatcaaatg 240
atacatagta ccaagtcctc ttctgtgaag ctgcct 276

<210> SEQ ID NO 44
<211> LENGTH: 475
<212> TYPE: DNA
<213> ORGANISM: Mouse

<400> SEQUENCE: 44
agtctggagt cacttggaac cagttatatt aagcacttac attgtgatta aaaaaaaagc 60
acaaatatgc ttcttttatc ttttaaaaaa agttctcata tggtacccct attattcatt 120
gagtagagca taaattcagc catcctttcc tctgcttgtt atttggatga ttgttttctt 180
tcttttcttt ctttctttct ttctttcttt ctttctttct ttctttcttt ctttctttct 240
ttctttcttt ctttctttct ttctttcttt tttgagacag ggcttttctg tgtaagcttg 300
ccgccttctg tacttcacta cctcccagct attaccttga ctcacccatt acgtctcagg 360
aaacctttct tggccccaca taaagaattt ggtttatgaa gatgcatgct actatagtta 420
cttacaacat cacactactt aattgaaaat aaaagtttgg ttgtccacgt cttgg 475

<210> SEQ ID NO 45
<211> LENGTH: 392
<212> TYPE: DNA
<213> ORGANISM: Mouse

<400> SEQUENCE: 45
tccctgattg cttttcctcg tggtgtttaa aacacatata tgcaggcaaa acatccacat 60
acattaaaaa aaataataag aaagaaagaa aggaagaaag aaagactaag aaagaaggaa 120
agaaagaagg aaagaaagaa agaaagaaag aaagaaagaa agaaagaaag aaagaaagaa 180
agaaagaaag aaagaaagga aggaaggaag ctgcttacat ttggacaatt tgaattgatt 240
ttataaggtg aattttcttt aataagtcac caaattagat atattgagta cttaaacaca 300
tatgcatgca tatacatata tagtctgtgg cttatctctg atttatcttg catacacctt 360
cctgttaaca ctatgtcagc ctcaaaatgc ca 392

<210> SEQ ID NO 46
<211> LENGTH: 241
<212> TYPE: DNA
<213> ORGANISM: Mouse

<400> SEQUENCE: 46
agtgggccag agaacttgga agggttagaa gctctgtgac tctcctcccc atttttttctt 60 tctttctttc tctctttctt tctttctttc tttctttctt tctttctttc tttctttctt 120
tctttctttc tttctttctt tctcttccca ctggctaagc taagtctcct agtggacccc 180
taaacagata tgcttctgtg taaaaaaaaa aaaaaaaaaa tctcagtgtg gaccagtatg 240
g 241

<210> SEQ ID NO 47
<211> LENGTH: 226
<212> TYPE: DNA
<213> ORGANISM: Mouse

<400> SEQUENCE: 47
ggggtggttg agtggcttta aaatgactga ataccactca ttgtgctgga taagaaagaa 60
agaaagaaag aaagaaagaa agaaagaaag aaagaaagaa agaaagaaag aaagaaagaa 120
agaaagaaag aaagaaagac gaaaaccgac aaactgcagt ggaaataaat acagcattgc 180
aggttggtgt gtgaggctac agctggggaa gccagggctg ttaagt 226

<210> SEQ ID NO 48
<211> LENGTH: 328
<212> TYPE: DNA
<213> ORGANISM: Mouse

<400> SEQUENCE: 48
agagcatgcg atgtcttggc tagaccatag tttgaaaagc tttgttatca gtgggcagtt 60
ttctatgtat tgctgcttct taacttctaa attctcttca gttctttggc tgctgcatcc 120
tttctcattc tctttaggtt tgtaccttaa ataaaatctg atacaactcc tttctttctt 180
tctttctttc tttctttctt tctttctttc tttctttctt tctttctttc tttctttctt 240
tctttcgttt atataaccac aggaagcagc ttcgattgac agattgtctc cagataccaa 300
aaagctataa actgtcagac accccaca 328

<210> SEQ ID NO 49
<211> LENGTH: 345
<212> TYPE: DNA
<213> ORGANISM: Mouse

<400> SEQUENCE: 49
gggtgtagct tgtgttcagc tgcagatcaa gttcttgggc tttctttcct tctttccttc 60
tttccttctt tccttctttc cttctttcct tatttccttc tttccttctt tctttccttc 120
tgtccttcct tccttccttc cttccttcct tcctaacttc tttccttcct tccctccctt 180
cttccctctt tcttccttcc tttctttctt tctttctttc tttctttctt tctttctttc 240
tttctttctt tctttctctt tgaagatgga tattactccc cagatggagt aggtttggac 300
tctcattccc tcctttctca tgtaactaga aggcccaatc atggg 345

<210> SEQ ID NO 50
<211> LENGTH: 369
<212> TYPE: DNA
<213> ORGANISM: Mouse

<400> SEQUENCE: 50
acaccccctc atttttgtgg tatgtgtatg caaatggaag aagacctata tgagaaatta 60
tgggtatgaa gcccataagc caagcttatg ttttatttct caggcatcat ctatctacca 120
tttctttctt tcttccttcc tttctttttc tttctttctc tctctctcct ttctttcttt 180
ctttctttct ttctttcttt ctttctttct ttctttcttt ctttctttct taacagctga 240
gaaagtgtgg agatattcag tctagctggc cagagatcca aatgattgtc tttttcacct 300
aggcctagga ttacagagga agctaagcat gatgactttg tatatgagca ctgagagtga 360
aactctggt 369

<210> SEQ ID NO 51
<211> LENGTH: 171
<212> TYPE: DNA
<213> ORGANISM: Mouse

<400> SEQUENCE: 51
aaaggaggcg agtagggtga cattactgtc ctaaaaatca agactctttc tttctttctt 60
tctttctttc tttctttctt tctttctttc tttctttctt tctttctttc tttctttctt 120
tctttctttc tttctatcac agaaaaaatg ctctcccatt gtgccacgta c 171

<210> SEQ ID NO 52
<211> LENGTH: 288
<212> TYPE: DNA
<213> ORGANISM: Mouse

<400> SEQUENCE: 52
ctagccagga aggagctctt gctgcccacc tacctacctc tccatctgca agcctgcctc 60
agtctcaggt gcacactggt ttgcccttgc cagctgcttg acaagcttct cgtgaattaa 120
gcagaattag aagaaagaaa gaaagaaaga aagaaagaaa gaaagaaaga aagaaagaaa 180
gaaagaaaga aagaaagaaa gaaagaaaga acccagagga agaactgggg atgtaggaag 240
cactacatcc tagagattaa attcaaattc tggcaattct ggctctgg 288

<210> SEQ ID NO 53
<211> LENGTH: 463
<212> TYPE: DNA
<213> ORGANISM: Mouse

<400> SEQUENCE: 53
ccccgtgctc attattctgc attataaaca acacttagga taatcaacaa cttactacca 60
gtcttatagt ccttaaataa ttaacatatt attcactagg ccaaggaata tggcctaaag 120
tttacagtaa taaaagagac agatgcaatt ttaagacaga aatgcaaagc tcttattctg 180
tttgttgggc taagtgaagt cacagctttt atcaaatgtt acttccactg atcttccttt 240
ctctttcttt ctttctttct ttctttcttt ctttctttct ttctttcttt ctttctttct 300
ttatttcttc cttccttcct tccttccttc cttccttcct tccttccttc cttcctctct 360
ctctctctct ctctctctct ctctctctct ctttctttct ttctttcagc acatgtccta 420
tgaagagcca caaagtatat aaatttgaag accaccgatg gcc 463

<210> SEQ ID NO 54
<211> LENGTH: 309
<212> TYPE: DNA
<213> ORGANISM: Mouse

<400> SEQUENCE: 54

```
tcagtctgca gcatggcata aatctggtag tacaggcctg tgatatgata ctggcactgc     60
caaaaagaaa gaaagaaaga aagaaagaaa gaaagaaaga aagaaagaaa gaaagaaaga    120
aagaaagaaa gaaagaaaga aaagagaaag agaaaatgtt cataaagagg gagaggagag    180
agagagagaa aaagagagag agagaacaca cgcaagaggg aaagactggt tgattgactc    240
aaaaagacct tcctggcctg cctgggttgg aatgtccgct gtagggcaga agggatgctt    300
ccaggcaaa                                                            309
```

<210> SEQ ID NO 55
<211> LENGTH: 372
<212> TYPE: DNA
<213> ORGANISM: Mouse

<400> SEQUENCE: 55

```
tctctgaatc catgagccgc ctctctagcg cccataactg ttccctaaaa atagaagtaa     60
aaagccaagt gtggtggcac tttaatacgt gggtctcagt gaattcaaga taagtctagt    120
ctacattgca atattggtct caaaaaaagg aaagaaggaa ggaaggaagg aaggaaggaa    180
ggaaggaagg aaggaaggaa ggaaggaagg aaggagagca acaaaagaaa gaaagaaaga    240
aagaaagaaa gaaagaaaga aagaaagaaa gaaagaaaga aagaaagaaa agaaagtttg    300
taatgagaat ccgagcgatc ccttgaaata aggaagtggg aaggaagact ctctcggtct    360
agtgtgctgc tt                                                        372
```

<210> SEQ ID NO 56
<211> LENGTH: 327
<212> TYPE: DNA
<213> ORGANISM: Mouse

<400> SEQUENCE: 56

```
tagagctctg gacagtgggg gctcctacac cctcatagca cagaattgtg tttgtcacct     60
tcactctgag cacttggcac tttctttctt tctttctttc tttctttctt tctttctttc    120
tttctttctt tctttctttc tttctttctt tctttctttc tttcttatgt ccaattctct    180
atgaactgta agcctcacaa atgtaatatg tatgtctttt atgtgctgaa tttgcacctg    240
tgctttatcc gtaggacgtt ttacattttg tccttcctac tcttggagtg tcctcttggg    300
gtgatatcaa gccccactga tcaggac                                        327
```

<210> SEQ ID NO 57
<211> LENGTH: 287
<212> TYPE: DNA
<213> ORGANISM: Mouse

<400> SEQUENCE: 57

```
cagcgtttct gcaaccagag gggatggtct ccaaaagaag acaagggatg ttttaaatat     60
aagaaagaaa gaaagaaaga aagaaagaaa gaaagaaaga aagaaagaaa gaaagaaagg    120
aagaaaggaa ggaaggaaga aagaaagaaa tctttgtttc ttcctaataa aaaataaaaa    180
caatcatatt cccagaagta tcttcatgtt ttccataggg aagcaccaga tactaccctg    240
acctgcctca tgatttctct cttctaagta tcctcacctg ctggtgg                  287
```

<210> SEQ ID NO 58
<211> LENGTH: 387
<212> TYPE: DNA
<213> ORGANISM: Mouse

-continued

```
<400> SEQUENCE: 58

tacaaggaac ccagagctgc cctgatgtgt ggtttctttt ctctttcttt ctttctttct     60

ttctttcttt ctttctttct ttctttcttt ctttctttct ttctttcttt ctttctttct    120

ttctttcttt cttaagattt atttatttat tttatgtgag tacagggtta ctgtcttcag    180

acataccaga agagggcatt ggaactcatt acaaatggtt gtgagccatc atgtggtttc    240

tgggaattga actcaggacc tctggaagag catttagtgc tcttaaccac tgagccatct    300

caccatcccc tgctttgtgg tttctaggtt gggagaatgc tgagagtctg tggtactggt    360

gcatctgagt ctcacagggc accttct                                        387


<210> SEQ ID NO 59
<211> LENGTH: 351
<212> TYPE: DNA
<213> ORGANISM: Mouse

<400> SEQUENCE: 59

tcccttttca ggctttgccc tcagatacag ttgatgcagg ttaattttat cctcccctct     60

tctgtcatag ttcttgttta tttgtaactt ctgttctccc tccatctctt ctccttggtt    120

tgttacattc tttgctgact ttacttcagt ttaacttcaa ctttggctgc cctaaactct    180

ttgtagtgcc caattgaaga aagaaagaaa gaaagaaaga aagaaagaaa gaaagaaaga    240

aagaaagaaa gaaagaaaga aagaaagaaa gaaagaggaa aggaacaaga acttattgat    300

tgctttttca tatcagttag tataaactga tcatccctgg tccagtctca g             351


<210> SEQ ID NO 60
<211> LENGTH: 190
<212> TYPE: DNA
<213> ORGANISM: Mouse

<400> SEQUENCE: 60

ctgacactct ccactctcgc acactccttc cttagagaaa gaaagaaaga aagaaagaaa     60

gaaagaaaga aagaaagaaa gaaagaaaga aagaaagaaa gaaagaaaga aagaaagaaa    120

gaagttgctc agggatttga tttactgatt acctgactgg cttagaaata ggtgggagac    180

tggatccttc                                                           190
```